United States Patent
Salinas et al.

(10) Patent No.: US 10,926,303 B1
(45) Date of Patent: Feb. 23, 2021

(54) METHOD AND APPARATUS FOR CLEANING A TUBE

(71) Applicants: Jose Salinas, San Antonio, TX (US); Paul Bryce Martin, Jr., San Antonio, TX (US)

(72) Inventors: Jose Salinas, San Antonio, TX (US); Paul Bryce Martin, Jr., San Antonio, TX (US)

(*) Notice: Subject to any disclaimer, the term of this patent is extended or adjusted under 35 U.S.C. 154(b) by 0 days.

(21) Appl. No.: 14/919,455

(22) Filed: Oct. 21, 2015

Related U.S. Application Data

(60) Provisional application No. 62/066,877, filed on Oct. 21, 2014.

(51) Int. Cl.
  B08B 9/043 (2006.01)
  B08B 9/027 (2006.01)
  A61M 16/04 (2006.01)

(52) U.S. Cl.
  CPC .............. B08B 9/027 (2013.01); A61M 16/04 (2013.01); *A61M 2209/10* (2013.01)

(58) Field of Classification Search
  CPC ... A61B 1/00135; A61B 1/00165; A61B 1/05; A61B 1/0669; A61B 1/267; A61B 1/2676; A61B 17/320725; A61B 1/00045; A61B 90/70; A61B 2090/701; A61B 1/0661; A61B 1/04; A61B 1/07; A61B 1/00142; A61M 16/04; A61M 16/0434; A61M 16/0463; A61M 16/0472; A61M 2202/203; A61M 16/0833; A61M 2209/10; B08B 9/027
See application file for complete search history.

(56) References Cited

U.S. PATENT DOCUMENTS

| | | | |
|---|---|---|---|
| 8,157,919 B2 | 4/2012 | Vazales et al. | |
| 8,381,345 B2 | 2/2013 | Vazales et al. | |
| 8,382,908 B2 | 2/2013 | Vazales et al. | |
| 8,458,844 B2 | 6/2013 | Vazales et al. | |
| 8,468,637 B2 | 6/2013 | Vazales et al. | |
| 8,534,287 B2 | 9/2013 | Vazales et al. | |
| 8,601,633 B2 | 12/2013 | Vazales et al. | |
| 2011/0023888 A1* | 2/2011 | Vazales | A61B 1/0669 128/207.14 |
| 2013/0023729 A1* | 1/2013 | Vazales | A61M 16/0463 600/104 |
| 2013/0030249 A1* | 1/2013 | Vazales | A61M 16/04 600/120 |
| 2013/0104884 A1* | 5/2013 | Vazales | A61M 16/0427 128/202.16 |
| 2013/0228196 A1* | 9/2013 | Vazales | A61B 1/126 134/8 |
| 2014/0150782 A1* | 6/2014 | Vazales | A61M 16/0434 128/202.16 |

* cited by examiner

*Primary Examiner* — Alexander Markoff
(74) *Attorney, Agent, or Firm* — Shah IP Law, PLLC; Samar Shah

(57) ABSTRACT

A cleaning tube may have an expansion portion that includes two or more slits. The cleaning tube may be deployed by linearly compressing the expansion portion, thus causing the tube to bulge into a disc through expansion of the slits. A sheath may cover the expansion portion to seal the slits. So deployed, the cleaning tube may be translated in a contaminated tube to remove contamination.

13 Claims, 6 Drawing Sheets

METHOD AND APPARATUS FOR CLEANING A TUBE

CROSS-REFERENCE TO RELATED APPLICATION

This application claims priority to U.S. Provisional Patent Application 62/066,877 entitled "Slit-Tube Technology and Endotracheal Tube Cleaning Application" filed Oct. 21, 2014, which is hereby entirely incorporated herein by reference.

FIELD

The disclosed method and apparatus generally relate to methods and apparatuses for cleaning a tube, and more particularly for the cleaning of body-inserted tubes, as well as to other methods and apparatuses for removing fluids, secretions and/or other materials from such tubes.

BACKGROUND

Tubes in a variety of industries and applications may become contaminated and require cleaning along the inside diameter of the tube. For tubes having one or more curves, the inside diameter may be difficult to access for adequate cleaning. In industries such as waste disposal, fluid transport, food and beverage manufacturing, health care, and materials handling, for example, proper cleaning of tubes is often required to satisfy health, safety and environmental regulations. In the health care industry, for example, tubes are used to convey various fluids, such as medicine, IV solutions, and to provide fluid or access channels, such as airways. In this case, tubes used in these environment will also become contaminated and require periodic cleaning to avoid potential complications with patients.

Patients having damaged or challenged airways due, for example, to trauma or pathology or the inability to breathe unaided, may require the placement of an endotracheal tube. An endotracheal tube is used to support the patient's ventilatory requirements after major surgery, trauma, or the development of severe medical conditions affecting the patient's ability to breathe.

Endotracheal intubation is a procedure that may be performed in a variety of clinical conditions and settings. It involves the placement of an artificial airway or endotracheal tube (ET tube) through the nose or mouth (orotracheal/nasotracheal tube) or directly through the trachea (tracheostomy tube) through a surgical procedure. The goal of an ET tube is to provide a clear path into a patient's lungs for proper intake of oxygen and carbon dioxide removal when the patient is connected to a mechanical ventilator. Patency of the ET tube is therefore essential to guarantee adequate gas exchange. However, since the ET tube is a foreign body, the airways may react by increasing production and buildup of mucus. These secretions have a tendency to accumulate and increase viscosity. Periodic cleaning of artificial airways or endotracheal tubes is considered the standard of care on patients that require endotracheal intubation and mechanical ventilation support in a hospital or critical care environment. The endotracheal tube may be coupled to a mechanical ventilator to aid the patient's respiration, and may remain in place for short periods or for extended periods of time, such as until the patient is able to breathe independently. Such periods of times may be for hours, days, weeks or months.

Secretions, debris, mucus, or other biological materials (biofilm) may thus accumulate on the inside wall of the endotracheal tubes. Such accumulation often occurs shortly after (e.g., within 24 hours of) initial intubation. Biofilms may contain harmful bacteria from which infection can originate. Thus, use of an endotracheal intubation may be a significant risk factor for infections, such as ventilator-acquired pneumonia. Such infections and attendant risks significantly increase patient morbidity rates, complications, number of ventilator days, and the cost of hospitalization.

Moreover, it may not be practical or clinically acceptable to change out the endotracheal tube due to buildup of biofilm, or remove the tube for cleaning. Removal and reinsertion of the endotracheal tube may add to patient discomfort, injure the airway, and decrease control of the airway during such process.

Thus, there exists a need for a method and apparatus for cleaning tubes in a variety of industries. In the health care industry, for example, there remains a need for an effective method and apparatus for cleaning body-inserted tubes, such as endotracheal tubes. Such cleaning may be required on a routine and preventative basis, or on an emergency basis.

SUMMARY

A cleaner for a tube may comprise a tube having a tube wall, and comprising a distal end and a proximal end; a plurality of normally-closed slits disposed in the tube wall, the plurality of slits being oriented generally along and disposed circumferentially about the central axis of the tube at the distal end thereof; and an actuator configured to compress the tube along its central axis so as to expand the slits, thereby causing the tube wall to bulge away from the central axis around the position of the said slits. A sheath may be disposed around the slits to seal the gaps created by the slits.

A method for cleaning an endotracheal tube may comprise inserting into the biofilm-coated lumen of an endotracheal tube the distal end of a tube comprising a tube wall and a plurality of normally-closed slits disposed in the tube wall, the plurality of slits being oriented generally along and disposed circumferentially about the central axis of the tube at the distal end thereof; compressing the tube along its central axis so as to expand the slits thereby causing the tube wall to bulge away from the central axis to form an expansion disc in contact with the endotracheal tube; and translating the tube in the endotracheal tube so as to scrape the expansion disc along the lumen surface and move the biofilm along the lumen.

DETAILED DESCRIPTION

Figure 1:
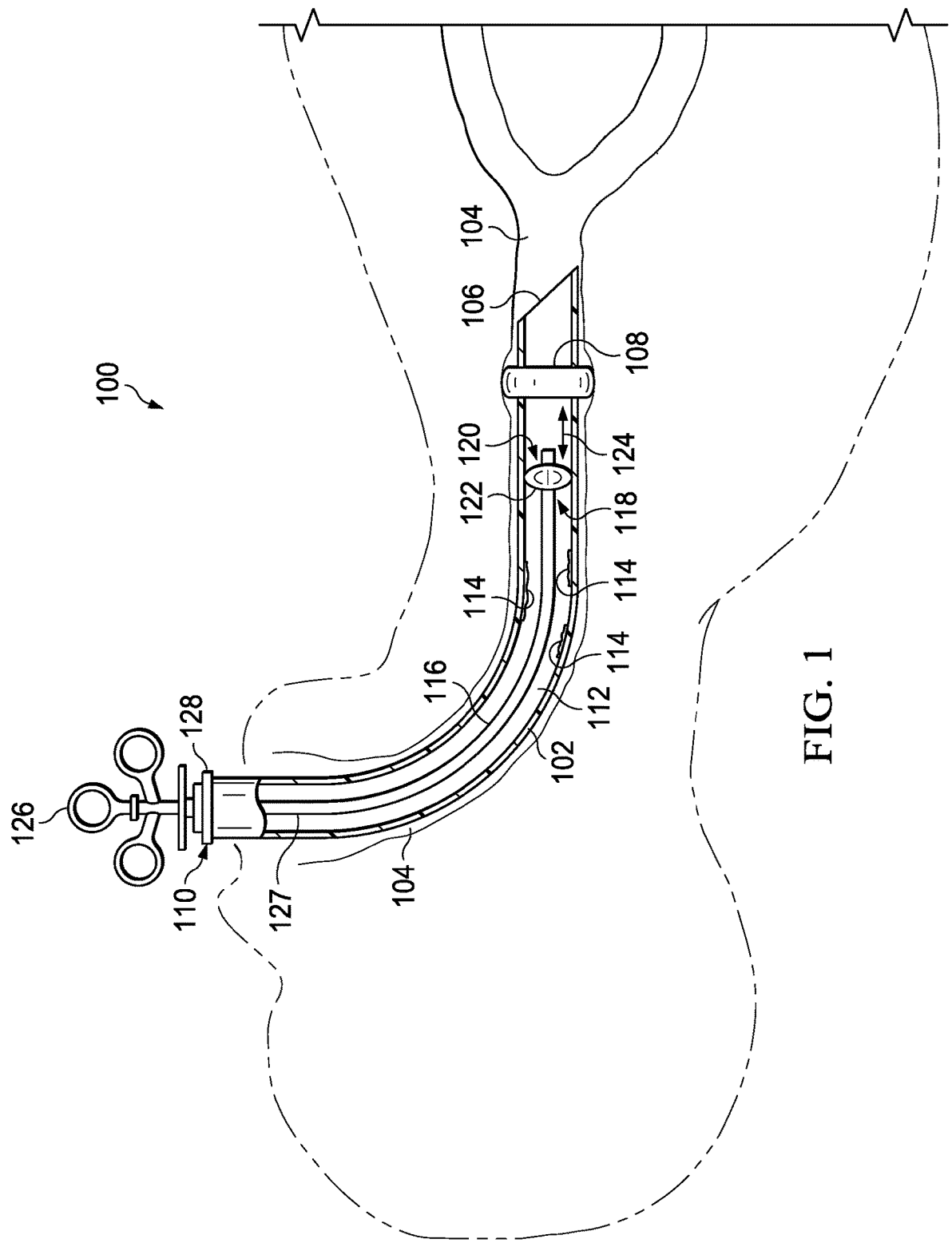
FIG. 1 illustrates one embodiment of a patient having an endotracheal tube and endotracheal tube cleaner.

As may be seen in the embodiment of FIG. 1, a patient 100 may have an endotracheal (ET) tube 102 inserted into the airway 104. The distal end 106 of the ET tube may have a balloon cuff 108 or other seal disposed so as to prevent gases from leaking back around the ET tube 102 and allow positive pressure ventilation. The proximal end 110 of the ET tube 102 may be coupled to a ventilator (not shown). The ET tube 102 may have a channel, or lumen, 112 disposed therein that may allow air or other gases to flow through the ET tube 102. Biofilm 114 may build up in the lumen 112.

A cleaning tube 116 may be disposed in the lumen 112. The cleaning tube 116 may be used to remove biofilm 114 and other secretions. The distal end 118 of the cleaning tube 116 may have one or more expansion portions 120 of the cleaning tube 116 wall configured to allow expansion of the cleaning tube 116. When expanded, the cleaning tube 116 may form a disc 122 at the expansion portion 120. The disc 122 may contact the lumen 112 wall and provide a surface with which to scrape biofilm 114 from the lumen 112 when the cleaning tube 116 is translated 124 in the lumen 112.

An actuator (not shown) may be used to expand and release the cleaning tube 116, thereby forming and collapsing the disc 122. The actuator may be manually operated through one or more handles 126 disposed at the proximal end of the cleaning tube. The proximal end 127 of the cleaning tube 116 may be coupled to the ET tube 102 by a collar 128.

Figure 2:
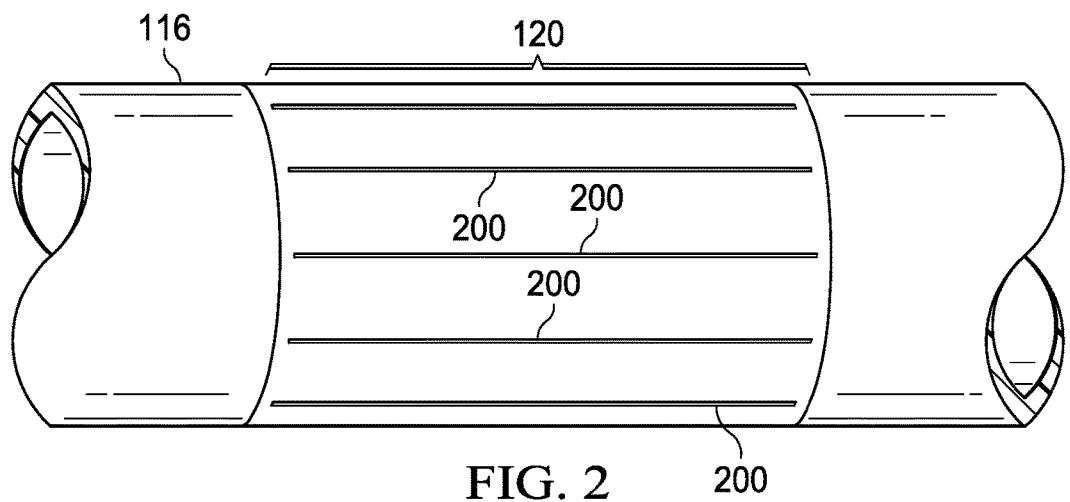
FIG. 2 illustrates one embodiment of the distal end of a tube cleaner.
Figure 3:
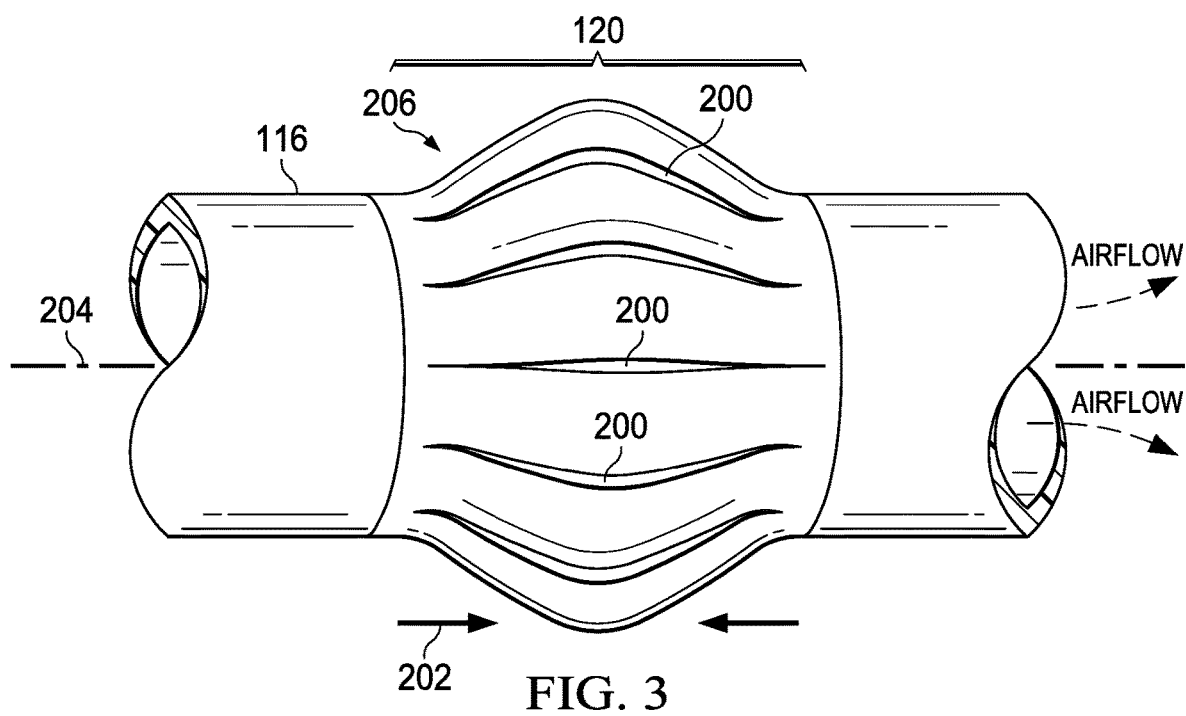
FIG. 3 illustrates one embodiment of the distal end of a tube cleaner in an expanded configuration.

As may be seen in the embodiment of FIG. 2, an expansion portion 120 of the cleaning tube 116 may comprise a plurality of slits 200. In this embodiment, the slits 200 may be disposed in the wall of the cleaning tube 116, and may be linear. The slits 200 may be disposed about the circumference of the cleaning tube 116. The slits 200 may be generally parallel. Any suitable number of slits may be used, such as two or more slits. When the cleaning tube 116 is actuated, the expansion portion 120 may be compressed 202 along the central axis 204 of the cleaning tube, as shown in the embodiment of FIG. 3. Such compression 202 may cause the wall of the cleaning tube 116 in the expansion portion to bulge outward away from the central axis 204 of the cleaning tube 116 by expanding the slits 200. The cleaning tube 116 may be compressed 202 so as to bulge the cleaning tube wall to any suitable diameter. The bulged expansion portion 120 may thus form a disc 206. The diameter of the disc 206 may be determined based on the length and configuration of the slits 200. Longer slits may allow the cleaning tube wall to bulge outward to a greater diameter than shorter slits. Thus, the cleaning tube 116 may be suitably configured for deployment in any tube diameter. Decompression of the cleaning tube may allow the expansion portion 120 to relax, thus collapsing the disc 206 after deployment. By use of a plurality of slits 200 in an expansion portion 120 of the cleaning tube 116, actuation of the cleaning tube 116 may allow gas, such as air, to flow through the cleaning tube 116 during deployment thereof. Thus, using such a cleaning tube 116 may avoid the need to remove the ET tube 102 during cleaning. In other embodiments, the cleaning tube may comprise a tube sealed at the distal end to prevent passage of gases through the cleaning tube during deployment. In yet further embodiments, the cleaning tube may comprise a solid rod having an expansion portion with slits as described herein. The expansion portion may comprise a tube disposed over the rod, or provided at the end of the rod, or as a section of the rod. For example, the tube may be removable mounted at the end of the rod.

Figure 4:
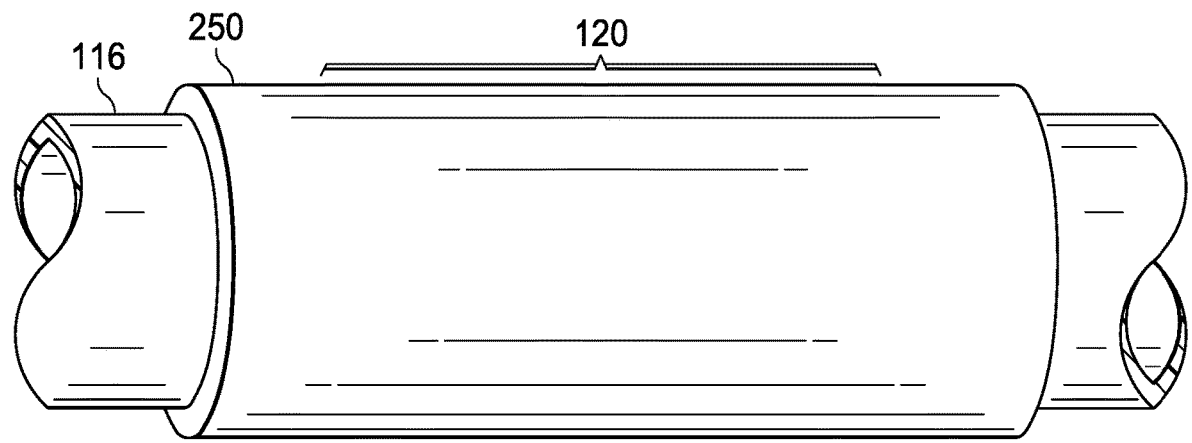
FIG. 4 illustrates one embodiment of the distal end of a tube cleaner having a flexible cover.
Figure 5:
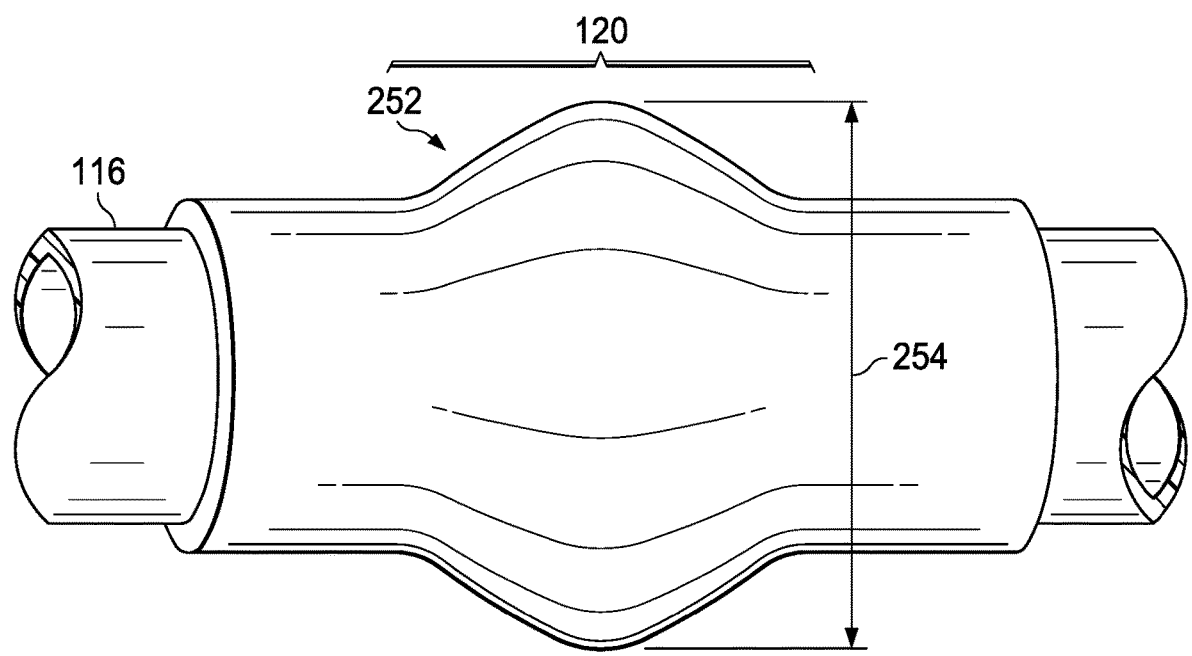
FIG. 5 illustrates one embodiment of the distal end of a tube cleaner having a flexible cover and in an expanded configuration.

As may be seen in the embodiment of FIG. 4, an expansion portion 120 of the cleaning tube 116 may be covered by a sheath 250. The sheath 250 may be sufficiently flexible to allow expansion as the expansion portion 120 expands into a disc 252, such as may be seen in the embodiment of FIG. 5. In some embodiments, the sheath 250 may seal the slits (not shown) so as to prevent gases from flowing through the slits even when the slits are expanded. The sheath 250 may also serve to provide a web of material over the expanded slits so that the outer diameter 254 of the expansion portion 120 remains substantially gap-free so as to better provide a sealing interface with the lumen of an ET tube. A sheath 250 may comprise any suitable flexible material, such as plastic, rubber silicone, and cloth. A sheath 250 may comprise a separate structure added to the cleaning tube, or may comprise a coating added to the cleaning tube, or may be formed as part of the cleaning tube.

In other embodiments, a sheath may be provided on the inside of the cleaning tube as an alternative or in addition to an external sheath 250. Such an internal sheath may similarly seal the slits so as to prevent gases from flowing through the slits even when the slits are expanded.

Figure 6:
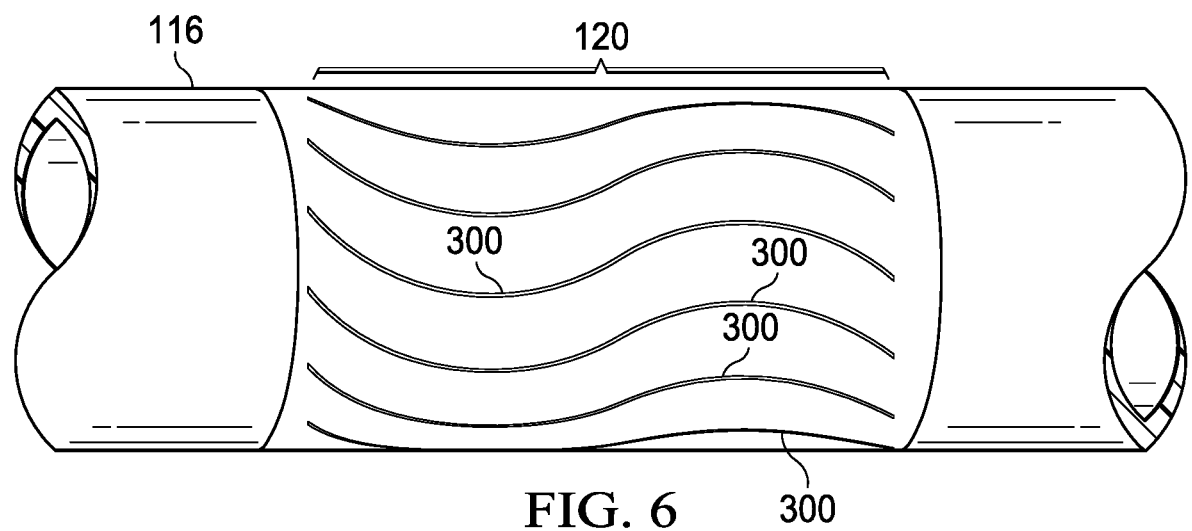
FIG. 6 illustrates another embodiment of the distal end of a tube cleaner.
Figure 7:
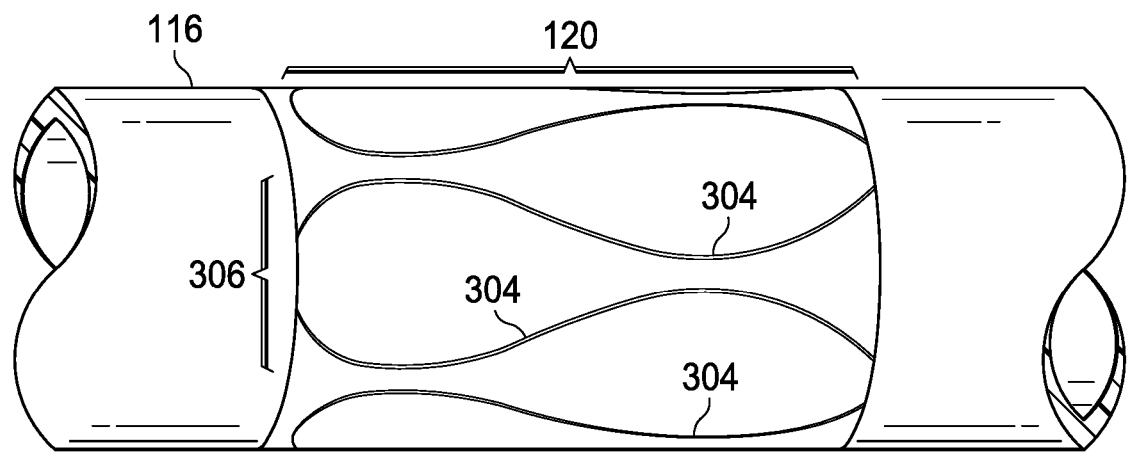
FIG. 7 illustrates yet another embodiment of the distal end of a tube cleaner.

In some embodiments, the slits may be formed by piercing the wall of the cleaning tube all the way through the thickness of the wall. The slits may comprise any suitable configuration, such as may be seen in the embodiments of FIGS. 6 and 7. In the embodiment of FIG. 6, the slits 300 may comprise one or more aligned curves. The slits 300 may be disposed generally in parallel about the circumference of the cleaning tube 116 at the expansion section 120. In the embodiment of FIG. 7, the slits 304 may comprise one or more mirrored pairs 306 of curves. The slits 304 may be disposed generally in parallel about the circumference of the cleaning tube 116 at the expansion section 120. A slit pattern may include linear slits, curved slits, or both linear and curved slits. Any suitable slit pattern may be used, such as may be desired to form a particular disc configuration.

Figure 8:
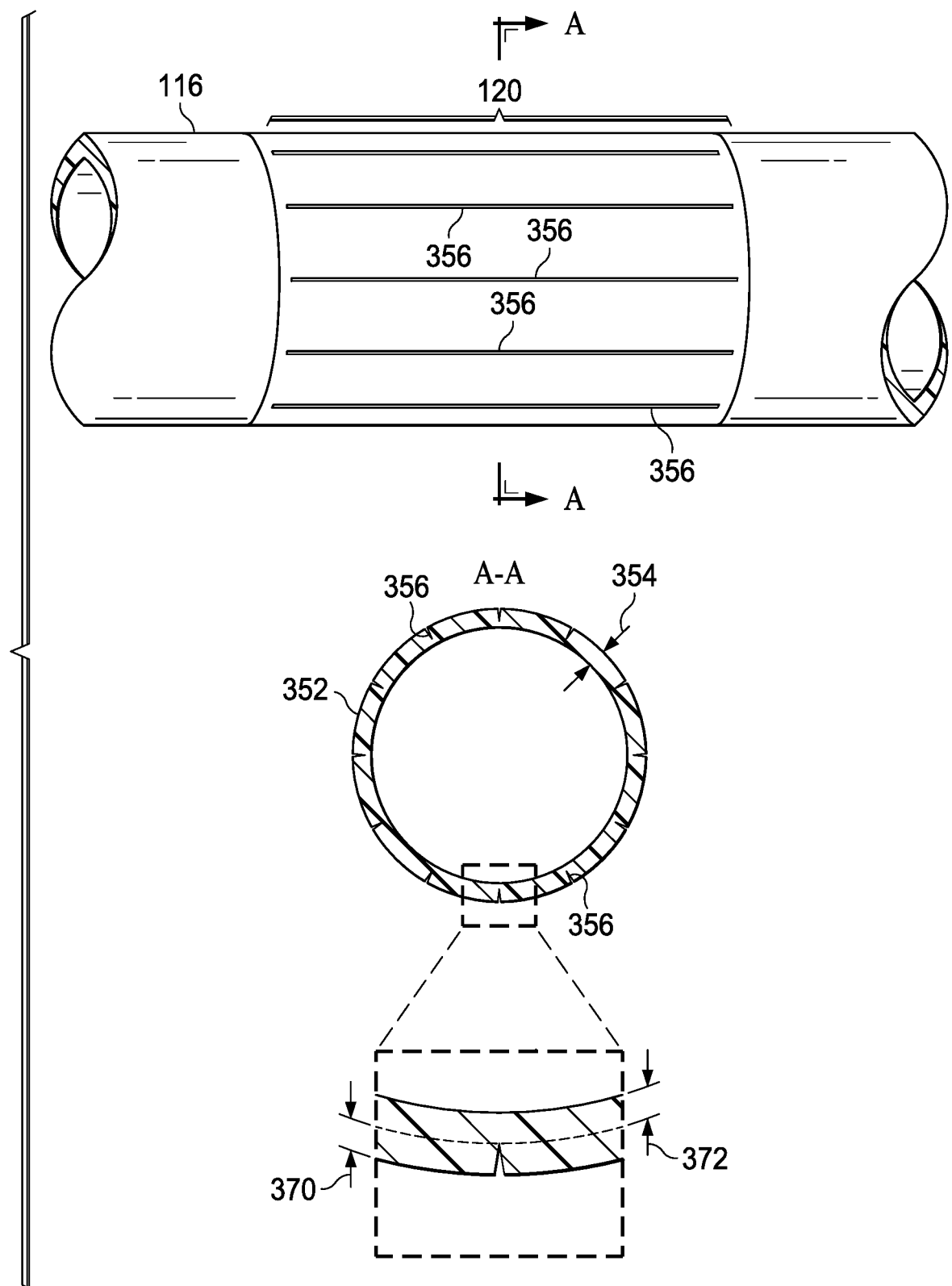
FIG. 8 illustrates one embodiment of a slit partially disposed through the wall of a tube cleaner.
Figure 9:
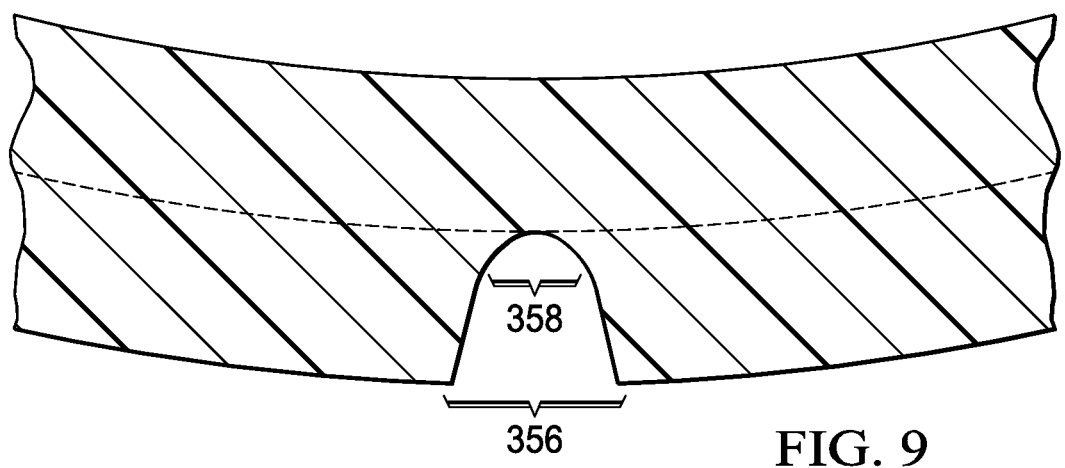
FIG. 9 illustrates the embodiment of FIG. 8 in which the slit is expanded.

In other embodiments, the slits may be formed by partially piercing the tube wall or cutting partway through the tube wall, as may be seen in the embodiment of FIG. 8. In a partial piercing embodiment, the tube wall 352 may comprise a thickness 354. Each slit 356 in the tube wall 352 may be cut partially through the wall to a slit depth 370. The remaining wall thickness 372 may thus be substantially less than the full wall thickness 354. The cleaning tube wall 352 may thus be weaker at the slits 356, and may allow the expansion portion 120 to expand into a disc (not shown) through expansion of the slits 356, yet still allow the slits 356 to remain sealed. The remaining wall thickness 372 may thus provide a thin web 358 of material in the expanded slit 356, as may be seen in the embodiment of FIG. 9.

A cleaning tube may be actuated by any suitable mechanism that provides a pushing, pulling, rotating or other actuating force, or any combination thereof. Such actuators may, for example, include an internal flexible cord, cable, rod, string, tube, threaded coupling, catheter or similar mechanism. For example, the expansion portion may have a distal ring at a distal end thereof having a flexible cord attached thereto. A user may pull the cord through the cleaning tube, thus urging the ring toward the proximal end of the tube, thereby linearly compressing the expansion portion and expanding the slits. In other embodiments, a flexible rod may be connected to a proximal ring at the proximal end of the expansion portion. A user may push the rod through the cleaning tube, thus urging proximal ring toward the distal end of the tube, thereby linearly compressing the expansion portion and expanding the slits. In such embodiment, a cord attached to a distal ring may serve to substantially secure the distal ring from translation in the tube to be cleaned as the proximal ring is urged toward the distal ring.

The cleaning tube may be formed from a typical catheter, or may be formed of any suitable structure or material. The cleaning tube may comprise plastic, metal, rubber, silicone, or any other suitable material. The cleaning tube may have any cross-sectional shape, such as round or polygonal. The cleaning tube may comprise an expansion portion that may expand into a disc having any suitable cross sectional area, such as roughly square (i.e., if four slits are used) or approximately round (if many slits are used). The disc may be configured to contact an entire circumference of a lumen or inner surface of a tube, or may contact only a portion thereof. A disc configured to contact an entire circumference of a lumen or inner surface of a tube may provide a sealed extraction path from the point of deployment in a tube (such as a fluid conveyance tube, a waste discharge tube, or an ET tube) to the outside of such tube. For example, for cleaning an ET tube, the cleaning tube may be deployed in a sterile (closed) environment so as to avoid the need to disconnect an ET tube circuit, thus avoiding patient exposure to a non-sterile environment.

The cleaning tube may comprise more than one expansion portion so as to provide multiple discs for scraping the inside of a tube. The simplicity of operation may permit use of the cleaning tube for routine cleaning as well as for emergency cleaning to remove any amount of biofilm build-up in a tube. The cleaning tube allows an ET tube or any other type of tube to be cleaned without use of negative pressure or suction. Translation of the cleaning tube in an ET tube allows biofilm to be removed out of the distal end or proximal end of an ET tube. The cleaning tube may include markings or graduations to allow a clinician to determine the degree to which a cleaning tube has been advanced into a tube to be cleaned, such as an ET tube.

A cleaning tube as describe above may be suitably configured for use in any body-inserted tube, and indeed any tube in which buildup may occur, such as in plumbing drain lines. Thus, the cleaning tube is not limited to use in ET tubes.

In a healthcare environment, for example, a cleaning tube as described herein may be connected as any closed-suction device between the ventilator circuit and the endotracheal tube during normal patient care. Depending on the institutional policies and procedures, for example, the device may be used multiple times a day for at least 72 hours of continuous use. When clinicians suspect severe airway obstruction caused by secretion buildup, the cleaning tube can be used as a rescue catheter without changing devices or altering the steps followed for routine airway clearance.

In the case of cleaning an ET tube, for example, a clinician may insert the distal end of a cleaning tube into an ET tube having a biofilm buildup. The distal end may be advanced into the ET tube a desired distance. The cleaning tube may be deployed by operating the actuator so as to linearly compress the expansion portion of the cleaning tube and cause the tube wall to bulge outward into a disc through slit expansion. Such compression may be effected until the disc expands to contact the inner diameter of the ET tube. The clinician may then translate the cleaning tube in the ET tube to push or pull biofilm out an end of the ET tube, such as the proximal end. The actuator may thereafter be released to allow the disc to collapse. The process may be repeated until the ET tube has been cleaned to a desired degree.

Although the disclosed subject matter and its advantages have been described in detail, it should be understood that various changes, substitutions and alterations can be made herein without departing from the invention as defined by the appended claims. Moreover, the scope of the claimed subject matter is not intended to be limited to the particular embodiments of the process, machine, manufacture, composition, or matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. For example, the cleaning device and methods disclosed herein may be used in a variety of industries, such as waste disposal, fluid transport, food and beverage manufacturing, health care, and materials handling, to name a few. Accordingly, the appended claims are intended to include within their scope such processes, machines, manufacture, compositions of matter, means, methods or steps.

We claim:

1. A tube cleaner comprising:
   a tube having a tube wall comprising a wall thickness, the tube comprising a distal end, a proximal end, and a central axis;
   a plurality of slits disposed on a portion of the tube wall, the portion of the tube wall having an expanded configuration and a collapsed configuration, wherein, in the expanded configuration, the plurality of slits are open and the portion of the tube wall bulges away from the central axis, and wherein the plurality of slits are closed when the portion of the tube wall is in the collapsed configuration; and
   an actuator configured to compress the tube along its central axis so as to urge the distal end toward the proximal end, thereby causing the plurality of slits to expand, and causing the portion of the tube wall to bulge away from the central axis and contact another tube's inner lumen,
   wherein the slits are formed by partially piercing the thickness of the tube wall or cutting partway through the thickness of the tube wall, so that a remaining wall thickness in the slits is substantially less than the wall thickness.

2. The tube cleaner of claim 1, wherein the diameter of the portion of the tube wall in the expanded configuration being determined by the length and configuration of the slits.

3. The tube cleaner of claim 2, wherein longer slits allow the portion of the tube wall to bulge outward to a greater diameter than shorter slits.

4. The tube cleaner of claim 1, further comprising a flexible rod, the tube being mounted to an end of the flexible rod.

5. The tube cleaner of claim 1, the actuator comprising:
   a distal ring mounted to the tube wall between the distal end of the tube and the plurality of slits; and
   a flexible cord attached to the distal ring and extending from the distal ring, the cord being accessible by a user when the tube cleaner is placed within another tube's inner lumen, the flexible cord urging the distal ring toward the proximal end of the tube when a user pulls the flexible cord, which thereby causes the tube wall to bulge away from the central axis at the plurality of slits.

6. The tube cleaner of claim 1, wherein the plurality of slits are generally parallel to each other and to the central axis, and are disposed about a circumference of the tube.

7. The tube cleaner of claim 1, wherein, in the collapsed configuration, an outer diameter of the portion of the tube wall is equal to an outer diameter of the tube.

8. The tube cleaner of claim 1, wherein the tube is an elongated tube, and wherein the portion of the tube wall comprising the plurality of slits is disposed near the distal end of the tube.

9. The tube cleaner of claim 1, wherein the plurality of slits are completely closed when the portion of the tube wall is in the collapsed configuration.

10. The tube cleaner of claim 1, wherein the tube is sized and shaped to be inserted into an inner lumen of an endotracheal tube so that the proximal end of the tube extends proximally of a proximal end of the endotracheal tube and the distal end of the tube is positioned proximally of a distal end of the endotracheal tube.

11. The tube cleaner of claim 1, wherein an entire length of the tube is made from one material.

12. The tube cleaner of claim 11, wherein the one material is plastic, silicone, or rubber.

13. The tube cleaner of claim 1, wherein, in the expanded configuration, the portion of the tube wall directly contacts the inner lumen of the another tube.

* * * * *